United States Patent [19]

Lee et al.

[11] Patent Number: 5,200,027

[45] Date of Patent: Apr. 6, 1993

[54] OIL MICROSENSOR HAVING INTERDIGITATED ELECTRODES WITH ROUGH SURFACES AND METHODS OF MAKING AND USING THE SAME

[75] Inventors: Han-Sheng Lee, Bloomfield Hills; Su-Chee S. Wang, Sterling Heights; Otto J. Klingenmaier, Warren, all of Mich.

[73] Assignee: General Motors Corporation, Detroit, Mich.

[21] Appl. No.: 790,401

[22] Filed: Nov. 12, 1991

[51] Int. Cl.⁵ .......................... B44C 1/22; C23F 1/00
[52] U.S. Cl. ..................................... 156/651; 73/116; 156/656; 156/659.1; 156/664; 437/187; 437/228; 437/245

[58] Field of Search .................. 73/116; 156/649, 651, 156/656, 659.1, 664, 665, 666; 252/79.1, 79.2, 79.5; 204/15; 437/187, 193, 194, 225, 228, 245

[56] References Cited

U.S. PATENT DOCUMENTS

| | | | |
|---|---|---|---|
| 4,975,390 | 12/1990 | Fujii et al. | 437/225 X |
| 5,049,517 | 9/1991 | Liu et al. | 437/228 X |
| 5,051,379 | 9/1991 | Bayer et al. | 437/228 X |

Primary Examiner—William A. Powell
Attorney, Agent, or Firm—Cary W. Brooks

[57] ABSTRACT

Disclosed is an oil sensor having roughened electrode surfaces to produce oil condition related output current or voltage from the automotive engine oil as it is used.

16 Claims, 4 Drawing Sheets

OIL MICROSENSOR HAVING INTERDIGITATED ELECTRODES WITH ROUGH SURFACES AND METHODS OF MAKING AND USING THE SAME

FIELD OF THE INVENTION

The invention relates to oil sensors, and in particular, to oil sensors having interdigitated two-electrode structure with rough surfaces and methods of making and using the same.

BACKGROUND OF THE INVENTION

Proper lubrication is essential to engine life. When engine oil is continuously exposed to high temperatures, high pressure and an oxidizing (combustion) environment, the oil will deteriorate and lose its lubricating effectiveness. To protect the engine the deteriorated oil should be changed.

Analytical techniques in laboratories, accurate but very time consuming, are used to examine the oil's condition. Other methods, such as measuring the dielectric constant change in the oil or recording the thermal history of the oil have been used for monitoring the oil's condition. These methods require the use of the same engine oil or assuming no engine malfunctions throughout the whole measurements.

Using two-electrode structure sensor to measure the electrochemical activities or to measure the conductivity changes of chemically modified oil have been tried by others. The selectivity of such prior structures is not sufficient to differentiate between a new oil and deteriorated used oil, and are thus unacceptable. This is because the reactants quantities in new and used oils are high. Both oils have chemically active reactants in them; such as detergents and ZDP (zinc dialkyldithiophosphate) in the new oils and acidic oxidation products and blow-by contaminants in the used oils. Using a smooth electrode sensor, the current collected from measuring both new and used oils are high. Hence, an ordinary two-electrode sensor, either in "parallel plate" or interdigitated structure, has difficulty in distinguishing between new and degraded oils of the same type because all electroactive species are collected with near equal efficiency.

As the oil is degraded, both the physical and chemical properties of the oil will change. Monitoring the changes, it is possible to correlate the remaining oil life with these changes. However, different brands of new engine oils have different additive packages in them. It is very difficult to find a key parameter which changes in the same degree when the oil is no longer effective to protect the engine. For example, as was described in U.S. Pat. No. 4,733,556, issued Mar. 29, 1988, entitled "Method and Apparatus for Sensing the Condition of Lubricating Oil in an Internal Combustion Engine", the dielectric constant of an oil was used as the monitored parameter because it changes as the oil degraded. It is known that the dielectric constant of different brands of oils differ from each other. Therefore, it is difficult to find a dielectric constant value at which all brands of oil are definitely bad. Another prior method of evaluating oil is to monitor the viscosity of the oil. Unfortunately, the viscosity of the oil changed drastically only after some important additives were consumed. Hence, it is not practical to use oil viscosity to determine the oil conditions.

Oil lubricants have been used to lubricate and cool components of operating machinery. Often, as the oil lubricant performs its functions it undergoes thermal-oxidation degradation. It is also known that the addition of additive packages to the lubricant enhance and prolong the lubricant's useful life. However, after extended use, the additives of the lubricant are consumed and the useful life of the lubricant ends. Extended use of the lubricant beyond its useful life results in excessive component wear and eventual failure of the machinery. Naturally, it would be desirable to determine the point at which a lubricant's useful life ends so that it may be discarded and replaced with a new lubricant to insure the continued, safe, non-damaging operation of the machinery. Although mechanisms for an evaluating properties of lubricants have been known, such as that disclosed by Kauffman in U.S. Pat. No. 4,744,870, a qualitative sensing mechanism, particularly useful for automotive lubricants, has heretofore been unknown. Further, Kauffman's mechanism requires the mixing of a lubricant, solvent, organic base and electrolyte to produce an analysis sample that is measured outside of the engine.

Oil sensors having two electrodes in an interdigitated pattern are known. In operation, these oil sensors are immersed in an engine oil, and a saw-tooth AC voltage is applied to the electrodes. An electrochemical current with its magnitude depending upon the oil condition can be collected by the sensor. Normally, the use of an interdigitated two-electrode structure sensor has associated problems in differentiating between new and used oil because both oils have large quantities of chemically reactive species that produce higher sensor current or higher voltage when the sensor current is converted to a voltage output through an electronic circuit.

This invention describes how to solve the selectivity problem of prior art oil sensors. A feature of the present oil sensor is that the electrode surfaces are processed to make them rough.

SUMMARY OF THE INVENTION

The invention includes the discovery that the sensitivity problem of differentiating between new and used oils, due to both oils having large quantities of chemically reactive species, can be resolved by roughing an oil sensor's electrodes. The invention includes the discovery that local field enhancement is created at the tips of an electrode having rough surfaces. The invention includes the discovery that the regional high field produced by the rough surfaces helps to lower the potential barrier for the chemical reaction and enhance the reaction rate at the oil/electrode interface. The invention includes the discovery that the first portion of the output voltage of an oil having a detergent in it can be suppressed by using electrodes with rough surfaces. A preferred embodiment includes an oil microsensor having interdigitated electrodes with rough surfaces.

In operation, the oil containing concentrations of light molecular weight species, such as fragmented moleculars in used oil, the enhanced electrode reaction also increases the sensor output current. However, when the oil contains abundant heavy molecules having low diffusivity such as detergent in new oils, the slow molecular diffusion will limit the increase of the output current of new oils. Consequently, the roughing of the sensor electrode surface results in increased sensitivity for degraded oil and suppressed unwanted signal for new oil.

With voltage applied to the sensor electrodes, the electrical fields near the tips of the roughened electrode surfaces will be enhanced and will have a higher than average electric field. This regional high field helps to lower the potential barrier for the chemical reaction and enhance the reaction rate at the electrodes. When the oil contains high concentrations of light molecular weight species, such as fragmented molecules in used oils, the enhanced electrode reaction also increases the sensor output current. However, when the oil contains abundant low diffusivity molecules, such as the detergent in new oils, slow molecule diffusion will limit the increase of the output current. Hence, roughening electrodes will result in increased sensitivity of the sensor for the electroactive degraded oil products but not change the sensitivity for the heavy molecules found in new oils. The invention also includes a method of making and using the electrodes and sensors as described or claimed hereafter.

ADVANTAGES AND RESULTS

The advantages of the sensor disclosed herein are: (1) insensitive to the oil brand used; (2) the sensor indirectly monitors the key parameters, such as the acid number of the oil and the thermal stability of the oil (measured by differential scanning calorimetry to determine the oxidation induction time); (3) its small size allows in-line measurement; (4) it has a short response time and can produce results in less than one minute; (5) it can be prepared by IC (integrated circuit) fabrication techniques; and (6) the sensor may be prepared by batch fabrication which means potentially low cost.

Oil sensors having roughened electrodes are capable of quantitatively sensing the useful life of oil particularly automotive oils used in automotive engines. Despite the fact that high concentrations of active species are present in both new and used oils, roughened electrodes are capable of distinguishing quantitatively between deteriorated oil, and new oil or still useful oil. Small but sharp tips on electrodes create electric field enhancement around them, which increases the charge exchange rate at the electrodes by lowering the potential barrier there. A roughened electrode produces an electric field enhancement of about two to about ten times the average electric field of smooth electrodes. For example, 5 volts applied between two smooth electrodes 5 microns apart may have an average electric field of $1 \times 10^4$ volts per centimeter. Then a rough electrode according to the present invention would have an electric field of about $2 \times 10^4$ to about $10 \times 10^4$ volts per centimeter at the tips or protrusions caused by roughening the electrode. Thus, an electric field enhancement is produced of about two to ten times the average electric field of smooth electrodes. Maintaining the high charge exchange rate at the electrode requires re-supplying the charge carriers to the electrodes through either diffusion or drifting by the electric field. Local field enhancement produced by roughing the electrode surfaces has little effect on heavy molecules, such as detergents and dispersants in new oils. These heavy molecules have low diffusivities and cannot respond to the demand of supplying more reacting species to the electrode. Light molecules, such as fragmented oil molecules, oxidation products, and engine blow-by contaminants in badly degraded oils have high diffusivities and can respond to the demand and supply more charges to the electrode. Consequently, the local electric field enhancement created at the roughened electrodes favors the collection of charge carriers in used oils resulting in higher sensor outputs as compared with new oils. The oil sensor having roughened electrodes has a current or voltage output with a magnitude that continually increases quantitatively with the continually decreasing useful life of the oil during use. The addition of fresh oil to used oil will not affect the ability to quantitatively or qualitatively determine the end of the useful life of the fresh/used oil mixture. Most importantly, the present invention allows the oil to be evaluated without the need to remove the oil from the equipment that it lubricates and without the need to add solvents, organic bases or electrolytes (such as lithium perchlorate) or to place the oil into an electrolytic cell (i.e., the oil measurement may be made in situ).

DETAILED DESCRIPTION

Figure 1:
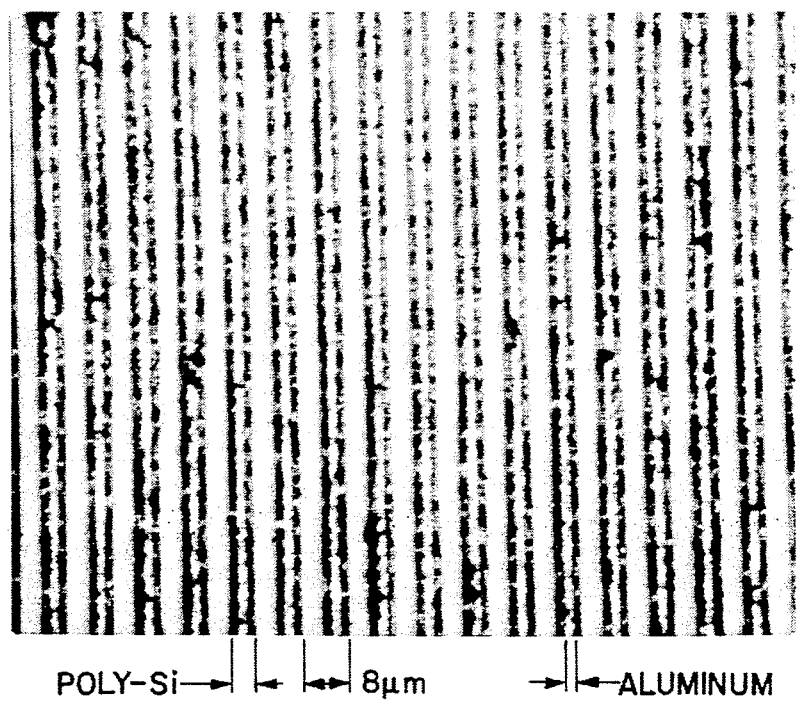
FIG. 1 is a photomicrograph of a finished sensor wherein the electrodes have been roughened by dipping the electrodes in a zincate solution for 25.5 seconds.

This invention involves the creation of rough electrode surfaces in an interdigitated structure. When there are sharp points (rough surface) on the electrodes, the electric field near the tips may be several times higher than the average electric field. The enhancement factor is a function of the geometrical shapes and is believed to have a value of 2 to 10 times that of smooth electrode sensors. This field enhancement will increase the charge exchange rate at the electrode/oil interface because the high electric field lowers the potential barrier for the electrochemical reaction at the electrodes. The major reactants in new oils are heavy, long-chain, low-diffusivity molecules with molecular weight more than 250, such as detergents and dispersants. Faster electrode reactions in new oil samples can only slightly increase the current collected by the electrodes because the supply of these carriers are limited by the slow diffusion. On the other hand, the oxidation products in the used oils are light, fragmented, short-chain molecules with molecular weight lighter than 125, which have higher diffusivities than the detergents. The fast diffusion of the reactants can maintain the higher charge exchange rate caused by the field enhancement resulting in higher steady state sensor current. Therefore, the result of creating rough electrodes is a high output in used oil but not in new oils.

Proper lubrication is essential to a life of any machine and in particular to automotive engines. When an automotive engine oil is continuously exposed to high temperatures, high pressures and oxidizing combustion environment, oil will deteriorate and loss it lubricating effectiveness thus requiring replacement of the automotive engine oil. There is a need for a sensor which can inform drivers about the condition of their automotive engine oil.

Oils useful in practicing the present invention vary greatly in their composition. These oils typically include electrochemically active species in addition to material acting only as lubricants. Electrochemically active species include detergents, dispersants, antioxidants and by-products of the same produced during the use of the oil to lubricate an engine. The amount of active species in an oil may vary greatly but for SG-type oil are typically present in an amount ranging from about 10 to about 20 weight percent of the oil. The active species may include at least one material selected from the group consisting of detergents, dispersants and additives for corrosion resistance, wear resistance, and antioxidant such as zinc dialkyldithiophosphate (ZDP). The detergents and dispersants perform the function of removing contaminants from the piston and cylinder wall surfaces. Generally, detergents include at least those compositions having alkaline earth metal ions and hydrocarbon chains. The molecular weight of the detergent may range from about 250 to about 2500. The amount of detergent in the oil may range from about 0.1 to about 5 weight percent of the oil. Generally, dispersants include at least those compositions having hydrocarbon skeletons with polar heads. The dispersant prevents contaminates from affecting the stability of the liquid phase. The amount of dispersant in the oil may range from about 0.1 to about 25 weight percent of the oil. Other additives, typically antioxidants such as ZDP may be present in an amount ranging from about 0.1 to about 25 weight percent of the oil. The antioxidant prevents oxidation of the base stock.

Preferred oils are automotive oils. Suitable commercially available automobile oils include for example Mobil 1, Sunoco Ultra, Quaker-State, Valvoline, Pennzoil, Mobil and Havoline. Preferably the automotive oils are SAE 5W-30, 10W-30, SF grade or SG grades.

The heavy molecules, i.e., having a molecular weight greater than 250, such as detergents and dispersants in new oil have low diffusivities and cannot respond to the demand of supplying more reacting species to the electrode. However, as the oil is used, the oil including these heavy molecules breaks down to produce light molecules, i.e., molecules having an average molecular weight less than about 125. Examples of these light molecules include fragmented oil molecules, oxidation products, and engine blow-by contaminants. These light molecules in badly degraded oil have high diffusivities and can respond to the demand and supply more charges to the electrode. Typically, the oil should be changed when: the oil has an acid number higher than 6; or base number lower than 2; or the oxidation induction time, measured at 175° C. with 550 psi pressurized oxygen ambient, shorter than 10 minutes or the water content higher than 2%; or fuel content higher than 3%; or the pentane insolubles content higher than 2%; or ethylene glycol content higher than 500 ppm.

New oils have chemically active reactants in them, such as detergents and ZDP (zinc dialkyldithiophosphate). Used oil have chemically active reactants in them, such as acidic oxidation products and blow-by contaminants. When the automotive oil is being used and degraded in an engine, the additives in the oil will be consumed and oxidation products will be produced. The oxidation products together with the engine blow-by contaminants are generally acidic in nature. With oil in an operating engine, the acidity of the oil will not increase initially because of alkaline additives, such as detergents, dispersants or anti-wear anti-oxidants (ZDP), can neutralize or surround the acidic products to make them chemically inactive. When the alkaline additives are low or near depletion and cannot effectively neutralize/surround the acidic products, the acidity of the oil (which can be quantified as the acid number) of the oil, will increase sharply. The alkaline additives and the acidic oxidation products are chemically active and responsible for contributing to the electric current collected by the oil sensor in an automotive engine.

When an oil sensor electrode having smooth surfaces is used in an automotive engine, the sensor current and consequently the sensor output voltage will initially increase slightly due to the consumption of the alkaline additives without significantly increasing the chemically active acidic products. Once the alkaline additives, either in reaction rate or in quantity, are low and cannot effectively neutralize/surround the acidic products, the sensor output voltage will reverse its trend and start to increase. A sensor output voltage will increase sharply when the oil's useful life is near the end or when the additives are depleted and are no longer able to neutralize the acidic products. Therefore, when plotting the two-electrode parallel-plate or interdigitated electrode sensor output voltage versus oil degradation time, an undesirable "V" shaped curve will be observed. The "V" shaped curve is undesirable because a "high" output voltage may be due to the presence of new/still useful oil or due to deteriorated spent oil. Consequently, one cannot determine quantitatively when the oil is no longer useful and should be changed. Further, as the engine is operated, oil is lost or evaporated and would need to be replenished but not require that all of the engine oil be changed. In such a situation, the addition of fresh oil would greatly complicate any attempt to determine when the oil should changed by tracking the "V" shaped curve produced by smooth electrodes.

The "V" shaped curve of the sensor output histogram can be improved to a desirable "check mark" or monotonic curve by roughening the sensor electrodes. The term "check mark" curve means without the addition of new (fresh or unused) oil, the data could fluctuate up and down but after fitting the data with a smooth curve, the lower arm value of the curve is at least 66% lower than the highest value in the high arm of the curve. The term "monotonic" with reference to the present invention means that for a given oil used, without the addition of new (fresh or unused) oil, that the output voltage from the oil sensor at a given time and a given oil temperature is equal to or greater than that at a preceding time. That is, the slope of an output voltage verses a measurement of oil use does not change from negative to positive but is either zero or positive as the oil is being used.

Figure 7:
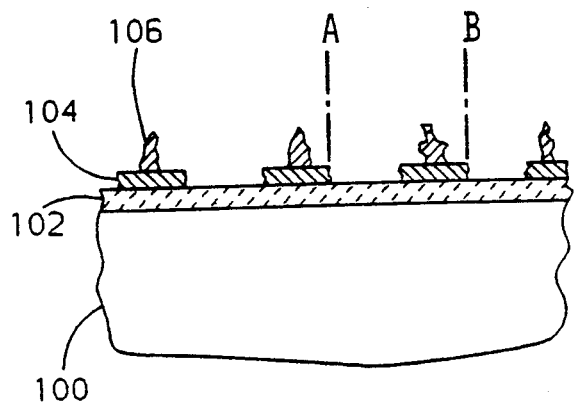
FIG. 7 is a side cross-sectional view of an oil sensor according to the present invention showing rough electrode surfaces.

An oil sensor according to the present invention may be prepared starting with a 76 millimeter diameter silicon wafer. As illustrated in FIG. 7 may include a silicon substrate 100; an insulating layer 102 which may be $SiO_2$, $Si_3N_4$ or $SiO_2$ and $Si_3N_4$; optionally a layer 104 for promoting adhesion of the electrode and may be, for example, a polysilicon layer; and an electrode 106 having rough surfaces. The electrode may be prepared from an electrically conductive material. Preferably the electrode includes at least one material selected from the group consisting of aluminum, copper, silver, nickel or gold. The distance between points A and B may preferably be about 8 μm. This corresponds to the photomicrographs of FIGS. 1–3, which shows a roughed relatively small white line which is the electrode, a black portion surrounding the electrode which is the polysilicon layer. The relatively larger white portion is the insulating layer.

Silicon dioxide may be thermally grown on the wafer followed by silicon nitride and polysilicon deposition. Typical thicknesses of these films is 0.5 μm, 0.15 μm, and 0.2 μm for $SiO_2$, $Si_3N_4$ and polysilicon, respectively. A material such as aluminum or other conductive materials so long as the material can be made rough, may be evaporated or deposited on the polysilicon and then the interdigitated pattern may be formed by standard photolithographic methods. The sensor may have a size ranging from about 0.01 cm by 0.01 cm to about 10 cm by 10 cm, and preferably about 0.7 cm by 0.7 cm. Each finger of the electrode may have a width ranging from about 1 μm to about 100 μm and preferably 5 μm, a height ranging from about 0.5 μm to about 5 μm, and preferably about 1 μm, and a length ranging from about 0.01 cm to about 10 cm, and preferably 0.7 cm. Smaller electrodes are generally preferred because they cost less to mass produce and can be used for in-situ measurements. In general when the spacing between electrode is narrow, the height of the electrodes and the sensor area can be small and the vice versa.

The sensor electrode(s) may be roughened mechanically, or by etching, or by imparting wave energy on the electrode or by any other means. Preferably, the electrode is controllably etched in a chemical solution, for example, by dipping the electrodes in a zincate solution. A suitable zinc material may be selected from the group consisting of $Zn^{+2}$ and anions. The zincate solution may be aqueous and may contain from about 0.1 weight percent to about saturation of the suitable zinc material. A preferred zincate solution is available from Frederick Gumm Chemical Co. under the trade name Clepo Bondal. The effect of the roughing of the surface of the sensor electrode is illustrated in the following example.

Figure 8:
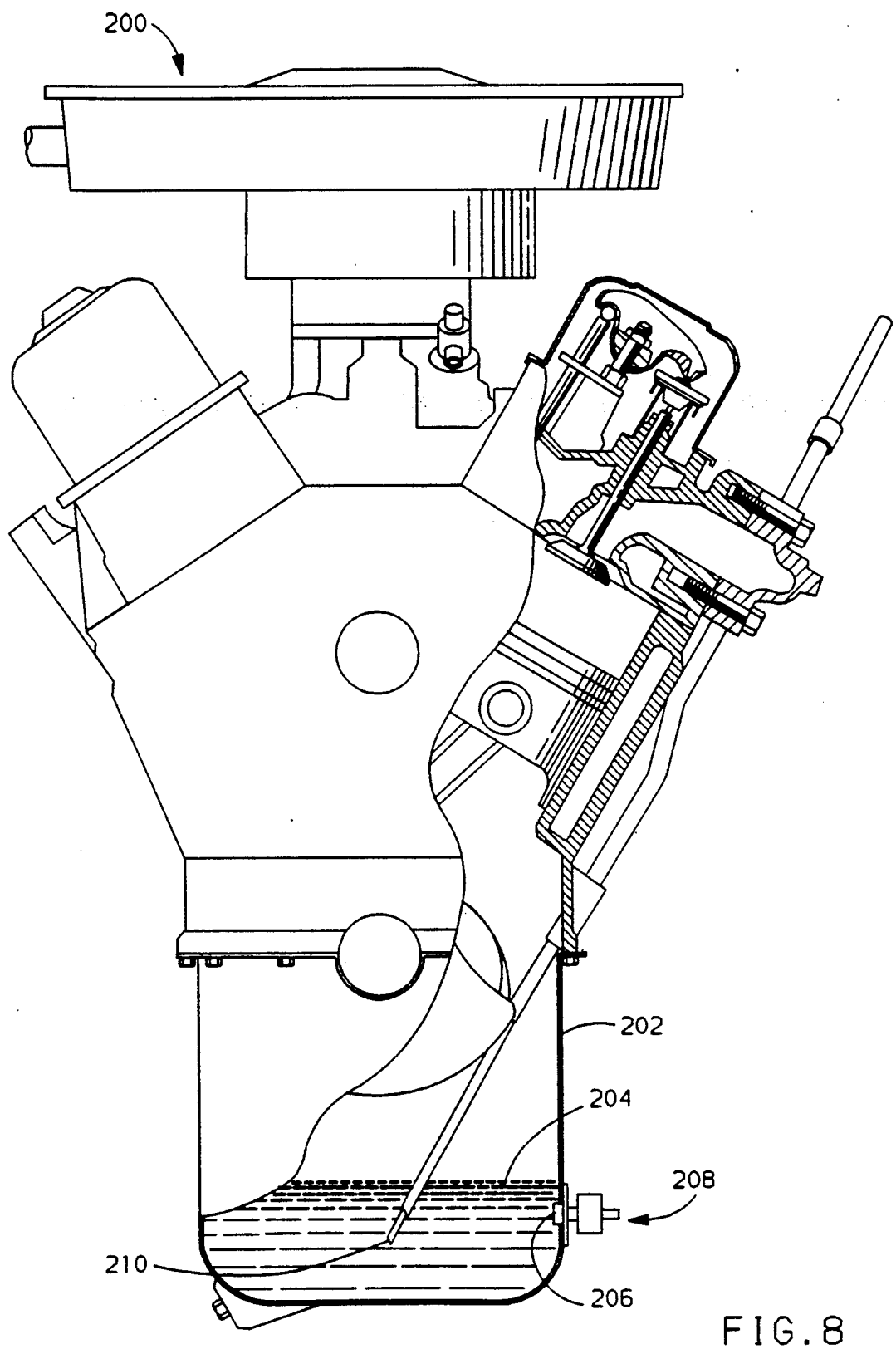
FIG. 8 is an illustration of an oil sensor according to the present invention positioned in an oil passage of an engine.

FIG. 8 shows an engine 200 having an oil reservoir 202 containing oil 204. The oil sensor may be positioned in any oil passage in the engine which would provide sufficient contact with the oil to allow the sensor to measure the oil. As shown in FIG. 8, the sensor 206 may be attached to the inside wall of the oil reservoir below the oil level and connected to a power source 208 in a manner known in the art. Another preferably position for the sensor is at the tip of the oil dipstick 210.

EXAMPLE I

An interdigitated aluminum electrode oil sensor may be prepared as described above and dipped in an aqueous zincate solution containing 80–100 g/l ZnO in 400–500 g/l NaOH. The dipping process starts with the bottom section of the interdigitated sensor entering the solution first. Five seconds later the middle section is dipped into the solution. After another 2.5 seconds, the top section is dipped into the solution also. The time in the solution for each zinc dip is 15, 10 and 7.5 seconds for each section of the wafer, respectively. After the dip, the whole wafer is put into a $HNO_3$ solution for 20 seconds to remove coated zinc. The $HNO_3$ solution may be aqueous and may contain about 0.1 volume percent to pure 15.4N $HNO_3$ solution and preferably 5 volume percent $HNO_3$. This zincate and $HNO_3$ cycle may be preformed three times and then the whole wafer may be given a three second quick dip in a zincate solution to cover the sensor with a very thin layer of zinc to minimize the growth of aluminum oxide on the electrodes. To increase the durability of the sensor, the sensor can be electroplated with chemically inert metal, such as gold. The wafer is diced into chips and made ready for testing.

Figure 2:
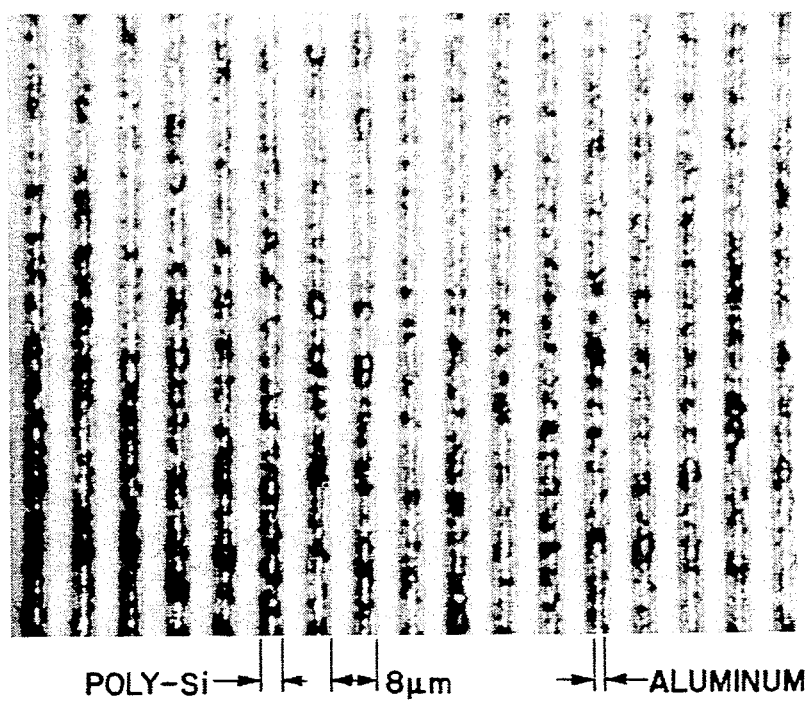
FIG. 2 is a photomicrograph of a finished sensor having the electrodes roughened by dipping the electrodes in a zincate solution for 33 seconds.
Figure 3:
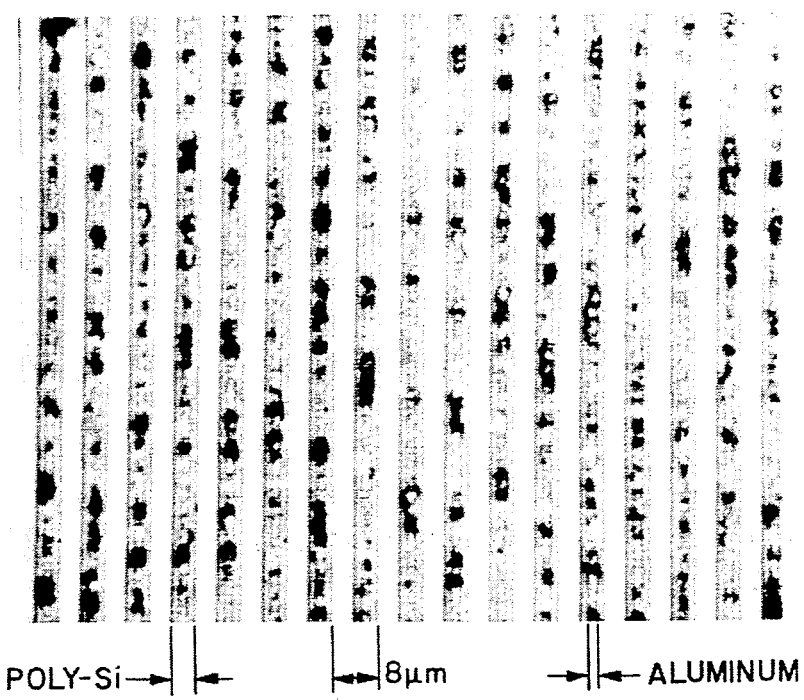
FIG. 3 is a photomicrograph of a finished sensor having the electrodes roughened by dipping the electrodes in a zincate solution for 48 seconds.

FIGS. 1–3 are photomicrographs of finished sensors of the three different sections of an interdigitated sensor prepared and treated as described above. The white portion of the electrodes in the Figure is aluminum and the black "shadow" is polycrystalline silicon. Each finger of an electrode has a matching interdigitated finger of the other electrode spaced approximately 5 μm apart from each other. A visual comparison of the photomicrographs of FIGS. 1–3 clearly shows and illustrates that the aluminum electrodes for the sensors in the zincate solution for the longer time (cycle representing a 15-second dip for each pass through the zincate solution) are thinner, narrower, rougher and more irregular in shape then those in the solution for shorter time periods.

The oil sensors so produced were evaluated using Mobil 1, SAE 5W-30, SG synthetic oil which had been degraded in automotive engine operating at ASTM IIIE conditions. The oil samples were drained from the automotive engine at 16 and 32 hours of engine operation. Based on oil analysis, the 32-hour oil sample was found to be near the end of its useful life. The oil analysis data indicated that the 32-hour sample had acid number increased from 3.5 (new) to 4.0, the base number decreased from 7.2 (new) to 5.7 and the oxidation induction time (pressurized oxygen and 175° C.) decreased from 98 minutes (new) to shorter than 10 minutes.

EXAMPLE II

To test the morphological effects on sensor selectivity, a fresh Mobil 1 oil sample was evaluated together with the two used oil samples.

Figure 4:
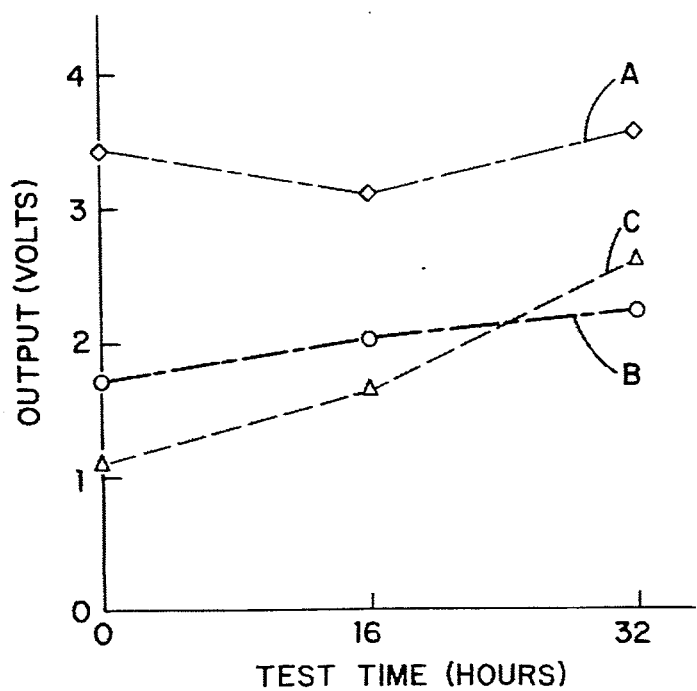
FIG. 4 is a graphical representation of a sensor output voltage for a different test-oil samples using electrodes with surfaces having varying degrees of roughness.

With the above prepared sensors immersed in the three different oil samples and the oil heated to 100° C. in an environmental chamber, a 50 Hz with ±5V peak AC voltage was applied to the sensor electrodes. The current collected by each sensor was amplified and rectified to a DC voltage output. The conversion factor was about 2.5 μA to 1 voltage output. The output voltages were plotted and are illustrated in FIG. 4. FIG. 4 shows a selectivity trend as a function of zincating time. In the upper section, for the sensor that was in the zincate solution for the shortest time, the sensor had a poor selectivity and produced a "V" shaped output voltage curve A. A monotonic increase in output voltage was observed on sensors in the middle (curve B) and bottom (curve C) sections where the sensor was prepared by dipping in the zincate solution the longest period of time (10 and 15 seconds in each zincate step, respectively).

In the above example, the only major difference between sensors from the different sections of the oil sensor so prepared is the morphology of the electrodes. The change of the electrode morphology from smooth to rough will increase the local electric field around the electrode. Since the field enhancement is localized in a short range, the rest of the region (i.e., this means the center region, at least 50% of the space between electrodes) will only have a small change. This is because with the high localized field, the voltage drop in that region which is the field times the short localized distance does not affect the voltage drop in the non-localized region too much. With the applied peak voltage of ±5V, the reaction rate at the electrodes is not high enough. The reacted charge carriers are re-supplied from the bulk oil through a diffusion process. Therefore, the system's output is proportional to the reactant concentration and the reaction rate at the electrodes.

When there are sharp points (rough surface) on the electrodes, similar to those in the bottom section, of the interdigitated sensor made by the above-described process, the electric field near the tips could be several times higher than the average electric field. This will increase the charge exchange rate at the electrode/oil interface because the high field lowers the potential barrier for the electrochemical reaction at the electrodes. The major reactants in new oils are heavy, long-chain, low-diffusitivity moleculars such as detergents and dispersants. Faster electrode reactions in new oil samples can only slightly increase the current collected by the electrode because the supply of these carriers are limited by their slow diffusion. The heavy mass of the large molecules is a limiting factor in responding to the increase of the reaction rate at the electrode surface. On the other hand, the oxidation products in the used oils are light, fragmented, short-chain molecules which have higher diffusivities and their size is not a limiting factor in their rate of reaction at the rough electrode surface. The fast diffusion of these used oil reactants maintain the higher charge exchange rate caused by the field enhancement resulting in higher steady state sensor current. Consequently, the use of rough electrodes produces a higher output voltage in used oils but not in new oils. As shown in FIG. 4, the sensor output changed from a "V" shape to a monotonic line when the electrodes were changed from smooth (top section of the sensor prepared by the above-described method) to rough surfaces (middle and bottom sections of the sensor prepared by the above-described method). The enhanced electrode reaction resulting in higher output voltage is clearly demonstrated in the oil sample taken from an automotive engine operated at 32 hours. When compared to the output from the middle section, the output voltage from the bottom section of the sensor is higher at 32-hour sample point, but exhibits lower output voltage for "newer" oils (0 and 16 hours oil samples).

EXAMPLE III

To further support that the electrode morphology plays a dominant role in improving the selectivity of the sensor, different materials were used in the final coatings. Thin layers of copper, gold, chromium and molybdenum were coated on electrodes prepared as described above with no noticeable change in sensor output.

EXAMPLE IV

Figure 5:
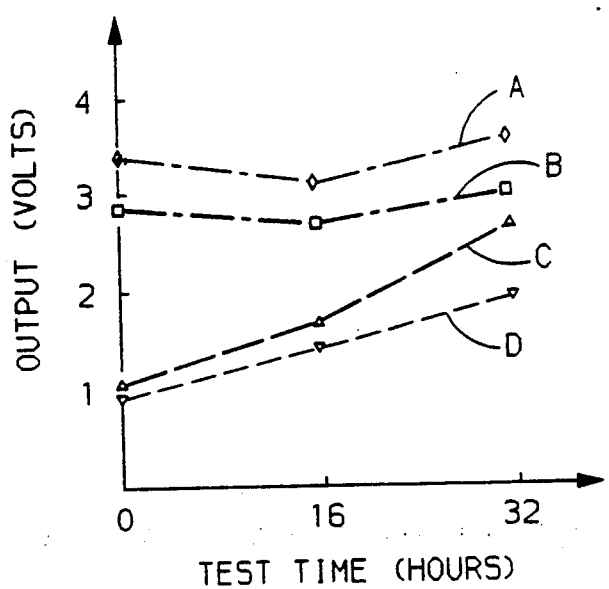
FIG. 5 is a graphical representation of the sensor output voltage at varying frequencies for electrodes having varying degrees of surface roughness.

This example illustrates the effect of frequency on the oil sensor. Since the sensor is equivalent to a capacitor in parallel with a variable resistor, the collected sensor current consists of displacement current and electrochemical current. At the same measurement frequency the displacement current component can be considered as a constant because the oil dielectric constant increased only slightly through degradation. If the measuring frequency has no effect on the collected electrochemical current component, higher frequency will merely shift the lower frequency results upward. The above-described oil samples were evaluated with a sensor prepared from the top and bottom portions of the above-described method at 20 Hz and 50 Hz. Lines A and B are top portion sensors at 50 Hz and 20 Hz respectfully, and lines C and D are bottom portion sensors at 50 Hz and 20 Hz respectfully. The output voltages were plotted and are illustrated in FIG. 5. Upon increasing the measuring frequency from 20 Hz to 50 Hz, the displacement current component from both the zero hour and 32-hour samples will be increased. However, at 50 Hz, not all the species which were active at the 20 Hz can contribute to the sensor current. The percentage of the electroactive species which cannot meet the demand caused by the higher measuring frequency is much higher in the fresh oil than that in the 32-hour oil sample. Hence, the enhanced electrode reaction produced by rough electrode surfaces (bottom section) resulted in higher output voltage in the 32-hour oil sample. The relatively smooth electrode (top section) exhibited the "V" shaped output curve for both 20 Hz and 50 Hz.

EXAMPLE V

Figure 6:
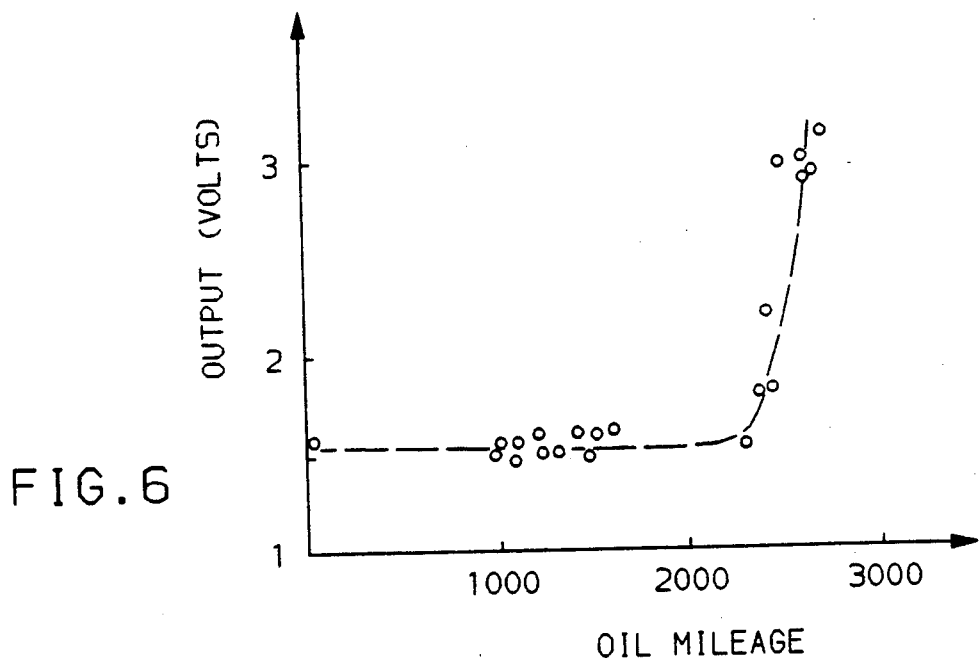
FIG. 6 is a graphical representation of a sensor output voltage of automotive oil in an automotive engine as a function of miles that the automobile was driven.

A sensor prepared from the bottom section of the above-described wafer was evaluated in a "real" environment by placing such a sensor mounted on a dipstick of a 2.0 L 1989 Corsica engine. The power supply which supplied the ±5V, 50 Hz saw-tooth waveform to the sensor was put inside the car. No temperature controlling or monitoring was attempted in the evaluation. The engine oil used in the car was Sunoco Ultra, SAE 5W-30, SG grade. The car was driven about 20 miles a day at 10 mile intervals from December 1989 to April 1990. Data were recorded just before stopping the engine. Because of the short driving distance, it is suspected that the engine oil was in the optimum oil temperature range of about 80°-120° C. for a short time only. Therefore, it was expected that the oil life would be shortened. The output voltage was plotted as a function of miles driven on a car as illustrated in FIG. 6. FIG. 6 shows a large increase in sensor output occurred at about 2500 miles of operation of the engine using the oil with the implication that the oil additives could not effectively neutralize the deteriorated product which resulted in the accumulation of active reactants and high output voltages. Hence, the oil was changed after the sharp increase in output, at about 2700 miles.

To verify that the oil was indeed deteriorated and needed changing, the 2700 mile oil sample was analyzed. The acid number, a quantitative indicator for the oxidation products and contaminants, of the used oil had increased from 1.7 (new oil) to 4.3. When oil has an acid number greater than 6, the oil is considered to be beyond its useful life. The base number, a measure of the remaining additives, decreased from 5.7 (new) to 2.7.

When oil has a base number less than 2, the oil is considered to be beyond its useful life. Even though both the acid and base numbers of the oils did not exceed the condemned limits, the acid number was higher than the base number implying the oil was too acidic and was not adequate to protect the engine. More critically, the oxidation induction time, measured at 175° decreased from 50 minutes (new) to shorter than 5 percent of the new oil value. Oxidation induction time was measured by differential scanning calorimetry. This method involves heating a few drops of oil in a high pressure oxygen atmosphere, 550 psi, and measuring the time required for the on-set of oxidation. A shorter oxidation time indicates less anti-oxidant, a key additive, remaining in automotive engine oil and reduced thermal stability. When oil has an oxidation induction time of less than 10 minutes, it is considered to be beyond its useful life. The oil analysis confirmed sensor's results that the 2700 mile oil was already deteriorated and could not effectively protect the engine.

The problems encountered in measuring the useful life of oil mainly arise from the presence of electrochemically active species present in the oils. Detergents, which often contain molecules having aromatic groups, are the most electrochemically active species. The second most electrochemically active species includes antioxidants such as ZDP which often contain reactive organic groups. Materials that do not appear to affect the electrode measurements of oil include dispersants, viscosity index improvers, and friction modifiers.

The embodiments of the invention in which an exclusive property or privilege is claimed are defined as follows:

1. A method of making an oil sensor comprising the steps of:
    growing silicon dioxide on a silicon wafer;
    depositing silicon nitride on the silicon dioxide;
    depositing polysilicon on the silicon nitride;
    evaporating a material comprising at least one selected from the group consisting of aluminum, copper, silver, nickel and gold, on the polysilicon to form a thin layer;
    forming an interdigitated pattern in said layer by photolithography to form electrodes;
    exposing the electrodes to a zincate solution comprising ZnO and NaOH; and
    thereafter exposing the electrode to an a $HNO_3$ solution.

2. A method as set forth in claim 1 wherein said step of exposing the electrodes to a solution of $HNO_3$ is for a period sufficient to remove the zinc coat produced after exposing the electrodes to a zincate solution.

3. A method as set forth in claim 1 wherein said step of exposing the electrodes to a solution of $HNO_3$ is conducted for a period of about 20 seconds and wherein said $HNO_3$ is 5 percent by weight of said $HNO_3$ solution.

4. A method as set forth in claim 1 wherein said steps of exposing the electrode to a zincate solution and a $HNO_3$ solution is preformed three times.

5. A method as set forth in claim 4 wherein the electrode is further exposed to a zincate solution for about three seconds so that a very thin layer of zinc forms on the electrode so as to minimize the growth of oxide on said electrode.

6. A product comprising the product-by-process of claim 1.

7. A method as set forth in claim 1 further comprising the step of electroplating the sensor with a chemically inert metal so as to increase the durability of the sensor.

8. A method as set forth in claim 1 wherein said step of exposing the electrode to a zincate solution is conducted for a period of about 10 to 15 seconds.

9. A method as set forth in claim 8 wherein said step of exposing the electrode to a zincate solution is repeated once.

10. A method as set forth in claim 8 wherein said step of exposing the electrode to a zincate solution is repeated twice.

11. A method of making an oil sensor comprising the steps of:
    growing silicon dioxide on a silicon wafer;
    depositing silicon nitride on the silicon dioxide;
    depositing polysilicon on the silicon dioxide;
    evaporating a material comprising at least one selected from the group consisting of aluminum, copper, silver, nickel and gold on the polysilicon to form a thin layer;
    forming an interdigitated pattern in said layer by photolithography to form electrodes;
    roughing the surfaces of the electrodes so that upon deploying said oil sensor in an oil comprising electrochemically active species, being used in an automotive engine, the end of the useful life of the oil is quantitatively determinable from the output voltage of said sensor.

12. A product comprising the product-by-process of claim 11.

13. A method as set forth in claim 11 wherein said step of roughing comprises etching.

14. A method of making an oil sensor comprising the steps of:
    growing silicon dioxide on a silicon wafer;
    depositing silicon nitride on the silicon dioxide;
    depositing polysilicon on the silicon nitride;
    evaporating a material comprising at least one selected from the group consisting of aluminum, copper, silver, nickel and gold on the polysilicon to form a thin layer;
    forming an interdigitated pattern in said layer by photolithography to form electrodes;
    roughing the electrodes an amount sufficient so that said sensor produces a monotonic output voltage or a check mark curve upon deployment in an oil comprising antioxidants and detergents as the oil is being used to lubricate an engine.

15. A product comprising the product-by-process of claim 14.

16. A method as set forth in claim 14 wherein said step of roughing comprises etching.

* * * * *